United States Patent
Scott et al.

(10) Patent No.: US 6,832,703 B1
(45) Date of Patent: Dec. 21, 2004

(54) MONOMER VIAL BREAKER

(75) Inventors: Christopher Scott, Hackensack, NJ (US); Anthony J. La Rosa, Wharton, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 34 days.

(21) Appl. No.: 10/441,758

(22) Filed: May 20, 2003

(51) Int. Cl.$^7$ ............................................. B26F 3/00
(52) U.S. Cl. ................. 222/189.06; 222/1; 222/541.6; 222/541.8; 225/93; 225/103; 241/99
(58) Field of Search ................................. 222/1, 189.06, 222/541.1, 541.6–541.9; 225/93, 103; 241/99

(56) References Cited

U.S. PATENT DOCUMENTS

| | | | |
|---|---|---|---|
| 2,977,014 A | 3/1961 | Kock | |
| 3,450,319 A | 6/1969 | Ray et al. | |
| 3,544,020 A | 12/1970 | Goldberg et al. | |
| 3,720,250 A | 3/1973 | Goldberg et al. | |
| 3,999,451 A | 12/1976 | Ogle | |
| 4,226,376 A | 10/1980 | Pfleger | |
| 4,353,869 A | 10/1982 | Guth | |
| 4,405,067 A | 9/1983 | Caron | |
| 4,405,069 A | 9/1983 | Vivier et al. | |
| 4,417,679 A | 11/1983 | Shields | |
| 4,506,817 A | 3/1985 | Parker | |
| 4,508,250 A | 4/1985 | Punchak | |
| 4,659,024 A | 4/1987 | Frunzi et al. | |
| D291,489 S | 8/1987 | Dudnyk | |
| 4,722,727 A | 2/1988 | Ogden et al. | |
| 4,896,649 A | 1/1990 | Rabenecker | |
| 5,129,566 A | 7/1992 | Ogden et al. | |
| 5,288,159 A | * 2/1994 | Wirt | ............................ 401/133 |
| 5,306,277 A | 4/1994 | Bryant et al. | |
| 5,423,440 A | 6/1995 | Castaneda et al. | |
| 6,099,532 A | 8/2000 | Florea | |
| 6,244,487 B1 | 6/2001 | Murray | |
| 6,257,474 B1 | 7/2001 | Jones et al. | |
| 2004/0062680 A1 | * 4/2004 | Kampa | ......................... 422/29 |

FOREIGN PATENT DOCUMENTS

EP      EA 1 031 333 A1     8/2000

* cited by examiner

*Primary Examiner*—J. Casimer Jacyna
(74) *Attorney, Agent, or Firm*—Lerner, David, Littenberg, Krumholz & Mentlik, LLP

(57) ABSTRACT

A cover for fracturing the neck of a glass ampoule or vial of the type having a glass body, a glass top and a glass neck joining the body to the top and dispensing fluid therefrom. The cover has a first portion with a hollow interior sized to sealingly receive and resiliently capture the body portion of the ampoule. The device has a second portion including a first hollow interior section sized to engage and capture the top of the ampoule. The second portion of the device has a second section in the form of a pouring spout in fluid communication with the ampoule neck and includes an opening for dispensing the liquid contents of the ampoule which opening is covered by a filter. A resiliently expandable portion connects the first and second portions. The expandable portion is in a contracted position before the neck of the glass ampoule is broken and expands upon breaking the neck thereby moving the top of the ampoule away from the ampoule body.

28 Claims, 11 Drawing Sheets

MONOMER VIAL BREAKER

BACKGROUND OF THE INVENTION

The invention relates to orthopedic bone cement. More particularly, the invention relates to a ampoule and dispenser for liquid monomer to be mixed with dry polymer as a cement component.

Orthopedic bone cement generally consists of a dry polymer component and a liquid monomer component which must be mixed together thoroughly and quickly before the cement sets. The monomer component is usually packaged in a standard glass ampoule: or ampoule which must be broken to release the monomer. The monomer must be dispensed quickly and mixed with the powdered polymer so that the cement may be properly prepared for use before it sets. In addition, glass fragments must be prevented from being dispensed with the monomer.

There are various known devices for facilitating the breaking of an ampoule and the dispensing of the ampoule contents. Many of these devices are not designed specifically for the dispensing of an orthopedic cement monomer component. Furthermore, many of the devices are complex and utilize vacuum chambers and transfer ampoules or suction tubes.

U.S. Pat. No. 3,450,319 relates to a polymeric flexible breaker for fracturing the neck of a glass ampoule.

U.S. Pat. Nos. 3,544,020 and 3,720,250 show safety devices in the form of a finger protection for grasping and breaking the end of a glass ampoule.

U.S. Pat. No. 5,129,566 relates to an ampoule holder and breaker which captures the ampoule body and which has a flexible portion, such as a bellows, portion for fracturing the neck of the ampoule.

U.S. Pat. No. 6,244,487 relates to an ampoule breaker that includes that a tip that is snapped off by a polymeric cap which is snapped over the top of the ampoule and has a fulcrum ring located at the neck of the ampoule.

U.S. Pat. No. 5,423,440 relates to a cap for resealing the ampoule which includes a protective sheath for sealing the top of the ampoule.

U.S. Pat. No. 6,099,532 relates to a disposable monomer dispenser and ampoule breaker having a portion which surrounds the body of the ampoule and a portion which engages the neck of the ampoule to fracture the same. The monomer dispensing portion of the holder includes a strainer such as a fabric mesh, to prevent glass particles from exiting the holder.

European Publication No. EP 1 031 333 relates to a device for fracturing the monomer ampoule and introducing the monomer into a powdered component.

U.S. Pat. No. 5,306,277 discloses a device which is specifically designed to break an ampoule and dispense a liquid monomer component of orthopedic cement. This device includes a syringe body adapted to receive an ampoule and break the neck thereof by wedging action against a portion of the syringe.

The device of the present invention is adapted to receive and at least partially cover a glass ampoule. The device is made of a polymeric material and is preferably placed on the glass ampoule prior to shipment. The polymeric cover performs a variety of functions, one of which is to prevent the user from cutting themselves when breaking open the glass ampoule. In addition, the polymeric cover provides some impact protection for the ampoule should it be inadvertently dropped. The cover or sleeve acts to reduce the chance of breakage by absorbing some of the impact.

The cover has an opening to pour the contents of the ampoule out after the neck of the ampoule is broken. The opening may include a mesh or screen which acts as a filter for ensuring that no glass particles are poured from the broken ampoule. Alternately, the opening may remain uncovered. This would be the case where the ampoule contains a therapeutic agent which is to be dispensed by a syringe. In this case, the therapeutic agent would be withdrawn via the syringe directly from the ampoule.

SUMMARY OF THE INVENTION

It is an object of the invention to provide a safe and simple device for opening a glass ampoule and pouring the liquid contents thereof out immediately prior to mixing with a second material.

It is an additional object of the invention to provide a breaking device which can sealingly engage the outer surface of a glass ampoule body, fracture the neck of the ampoule, move the top portion away from the ampoule body and allow the liquid to be poured out of the ampoule.

It is yet an additional object of the invention to provide a simple device for safely breaking the neck of a glass ampoule containing a liquid monomer which device filters any glass fragments out of the liquid being poured from the device.

These and other objects are achieved by a cover device for fracturing the neck of a glass ampoule of the type having a body, a top and a neck joining the body to the top. The ampoule cover is preferably made of a polymeric material, such as polyethylene or ethylene vinyl acetate (EVA), and has a cylindrical recess for engaging the cylindrical outer surface of the glass ampoule or ampoule body.

The cover contains a first portion having an interior sized to sealingly engage the body of the ampoule and a second portion having a first hollow interior section sized to capture the top of the ampoule and a second interior section communicating with the neck area of the ampoule. The second section receives the fluid once the neck of the ampoule is fractured and dispenses the same through an opening therein as the assembly is tilted. The opening has a mesh filter which traps any glass particles produced when the neck of the ampoule is fractured. The first and second portions of the cover are connected by a flexible portion such as an expandable bellows portion which is held in a contracted position on the ampoule when the top and body of the ampoule are connected. When the neck is fractured, the bellows portion expands to move the broken off ampoule top away from the ampoule body. The second interior section of the cover second portion remains in fluid communication with the neck area of the ampoule after it is fractured and the bellows expands, thus allowing the liquid in the ampoule to be poured from the opening on tilting the ampoule. Other flexible or moveable connection elements such as hinge type connection may be used to connect the first and second portions as long a those connection elements move the broken head away from the neck and out of the fluid flow path.

The first cover portion has a cylindrical hollow interior to engage the cylindrical outer surface of the body of the ampoule. The cover is made from a polymeric material such as polyethylene or EVA and is sized to sealingly engage the body of the ampoule upon insertion of the ampoule into the open end of the first portion. The cover may be placed on the ampoule prior to shipment or may be assembled to the ampoule intraoperatively. Since the first portion sealingly engages the ampoule body, a vent hole is provided in the area of the bellows, preferably on an upwardly facing surface thereof adjacent the first section of the second portion which captures the top of the ampoule. This enables the fluid to be easily poured from the second section of the second portion after the neck is fractured. The outer surface of the polymeric first portion may include ribs or ridges to enhance the gripping of the ampoule/cover combination. The first section of the second portion which captures the ampoule top has an interior shape conforming to the ampoule top and also resiliently engages the ampoule top to ensure that once the neck is broken, the top remains captured within the first section. In the preferred embodiment, the first section extends around the circumference of the ampoule top for more than 1800 and has an outer surface identical in shape to the inner surface which corresponds to the shape of the top.

While the breakable glass ampoule may contain a liquid bone cement monomer, the cover of the present invention may be used with any similarly shaped breakable ampoule or ampoule containing any fluid which requires the ampoule to be broken to be dispensed.

A method for opening a breakable fluid containing ampoule is also disclosed. Again, the ampoule has a top, a body and breakable neck portion connecting the top and the body. The method includes placing the cover over the ampoule, the cover having a first portion for receiving the ampoule body and a second portion for receiving the ampoule head and a flexible portion such as an expandable portion, connecting the first and second portions. The expandable portion is placed on the ampoule in a contracted state, being held in that state when the top is originally connected to the ampoule body. A lateral force is applied to the head, against the outer surface of the first section of the second portion of the cover to break the breakable portion or neck of the ampoule such as by using a thumb with the ampoule held in the user's hand. The ampoule top is automatically moved away from the ampoule body after the neck of the ampoule is fractured by the expansion of the expandable cover portion from its contracted state to an expanded state. The fluid in the ampoule may then be dispensed through the filter covered opening in the second section of the second cover portion.

These and other objects and advantages of the present invention will become apparent from the following description of the accompanying drawings, which disclose several embodiments of the invention. It is to be understood that the drawings are to be used for the purposes of illustration only and not as a definition of the invention.

DETAILED DESCRIPTION

Figure 1:
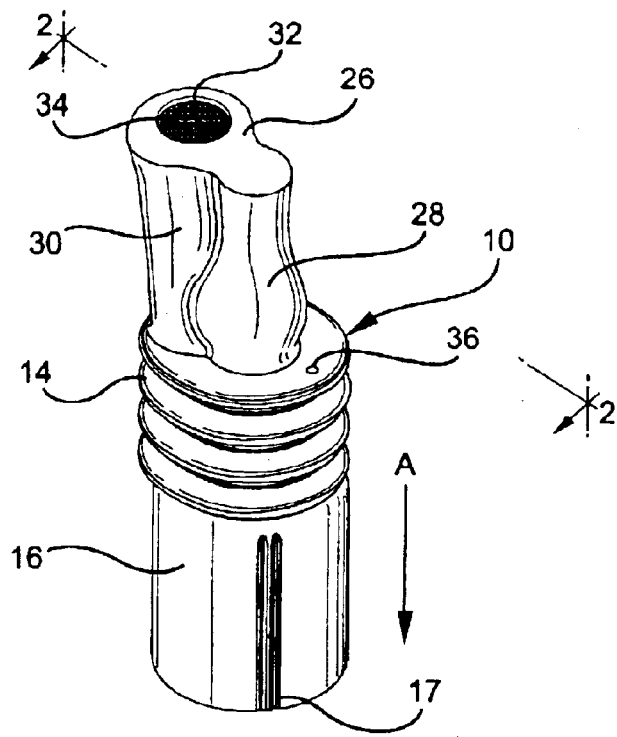
FIG. 1 is an exploded view of the vial or ampoule cover of the present invention prior to placement on the ampoule.
Figure 1:
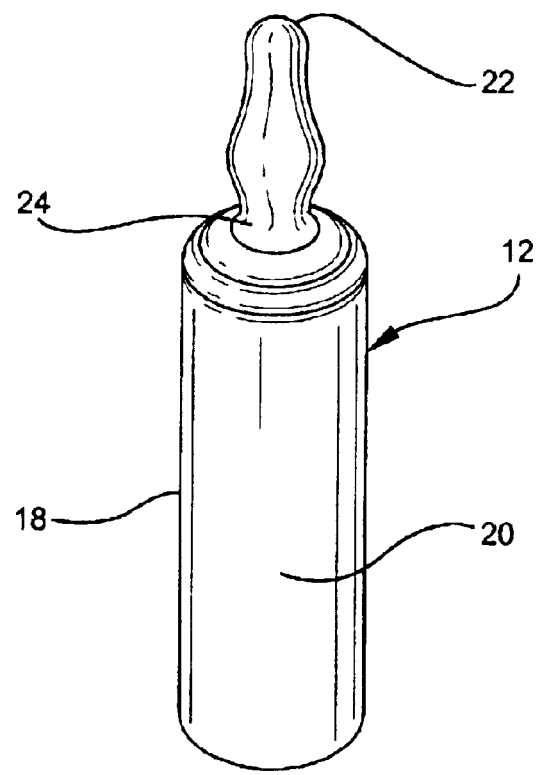

Referring to FIG. 1, there is shown a ampoule cover of the present invention generally denoted as 10 and a glass ampoule or ampoule generally denoted as 12 prior to assembly of cover 10 onto ampoule 12. In this position, a bellows or expandable portion 14 of cover 10 is in its relaxed or expanded state. Cover 10 includes a hollow tubular portion 16 adapted to fit on and capture the body 18 of ampoule 12. In the preferred embodiment, the ampoule body has a cylindrical outer surface 20. The ampoule has a typical head or top portion 22 which has an hour-glass shape. Portion 16 of cover 10 is made of a polymeric material such as polyethylene and is sized to tightly engage outer surface 20 of ampoule 12. Portion 16 can be made resiliently expandable to sealingly grip surface 20. Top portion 22 of ampoule 12 is attached to body 18 of ampoule 12 by a reduced neck area 24. Ampoule 12 is of a standard design and is well known in the medical art for dispensing liquid medicaments as well as for dispensing a liquid monomer of a two part bone cement system. Two part polymethylmethacrylate bone cements, for example, are well known in the orthopedic art.

Cover 10 further includes a second portion 26 which includes a first section 28 adapted to tightly engage top 22 of ampoule 12. Portion 26 of cover 10 includes a second section 30 immediately adjacent section 28 which can act as a pouring spout for the liquid in the ampoule. Section 30 includes opening 32 which, in the preferred embodiment, includes a screen or filter 34 which covers opening 32 and prevents glass fragments from the fractured ampoule from flowing out with the liquid contained therein. Screen or filter 34 may be a metal or plastic mesh and preferably a vinyl fabric and has openings and a thickness designed to allow the fluid to flow through the fabric but capture any glass fragments. The screen or filter 34 can be eliminated if a syringe is used td withdraw the fluid from the ampoule.

For ease of gripping and use, portion 16 of cover 10 may include a series of ribs 17 which are molded around the circumference of hollow cylindrical portion 16. For simplicity, only two such ribs 17 are shown. These ribs are optional and may be eliminated completely.

Figure 2:
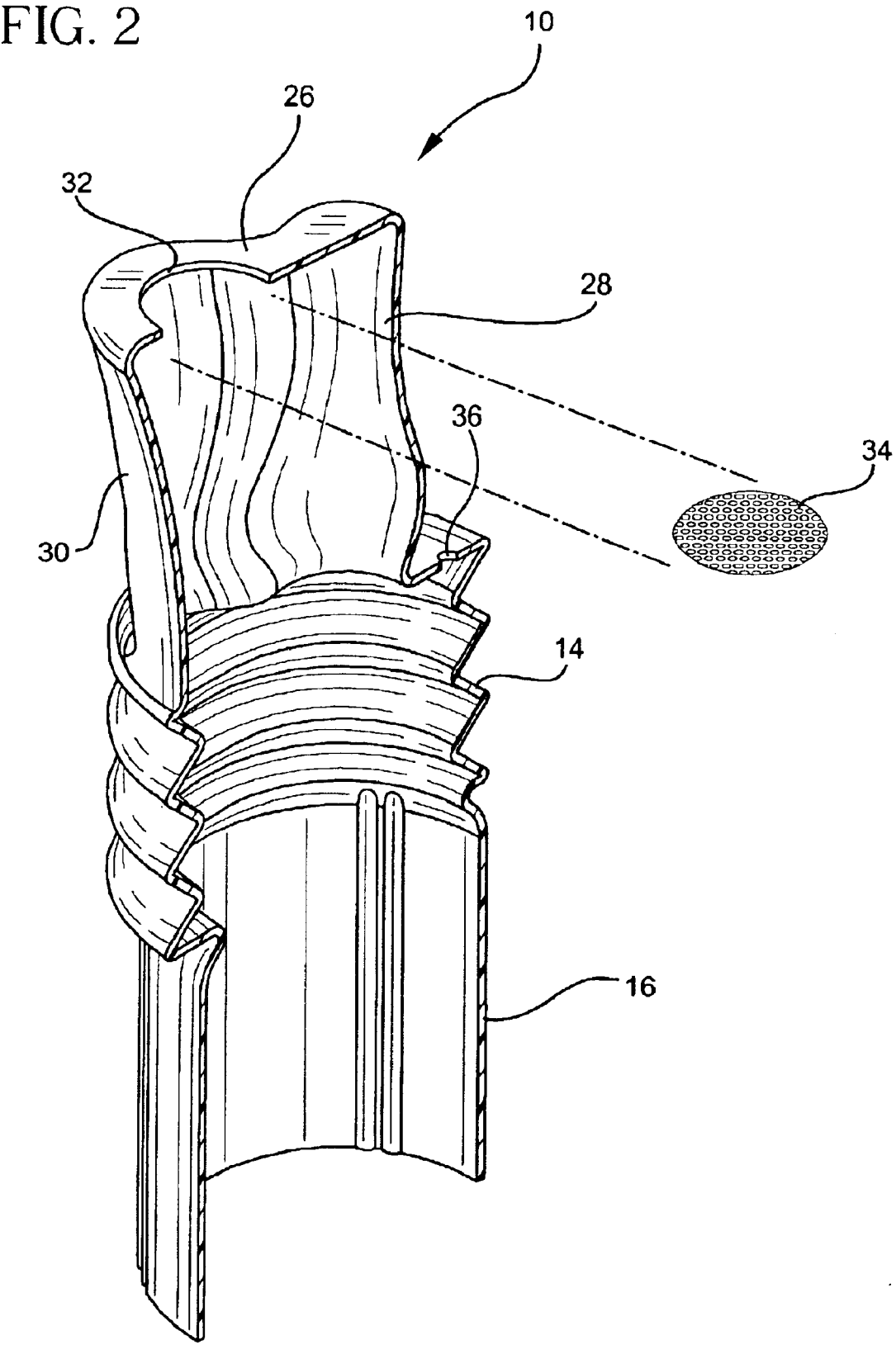
FIG. 2 is a sectional view of the cover shown in FIG. 1 along lines 2—2 thereof showing the mesh filter removed from the section.

Since portion 16 of cover 10 tightly engages outer surface 20 of body 18 of ampoule 12, a vent hole 36 is provided to let air enter the ampoule during pouring and to allow the bellows to compress, i.e., let the air with the bellows to escape during assembly. While in the preferred embodiment one vent hole is provided to allow air to flow both into the pour spout area and expandable bellows portion, more than one vent hole 36 can be provided. Referring to FIG. 2, there is shown a longitudinal sectional view of the cover 10 of FIG. 1, again with the expandable portion 14 in its expanded state. Expandable portion 14 is in the form of a bellows which may be compressed in a standard manner by applying a force to portion 26 thereof while portion 16 is held in place. In the preferred embodiment, the cover 10 is made of blow molded polyethylene or ethylene vinyl acetate. Also shown prior to assembly is the mesh filter 34 which is placed over opening 32, preferably from the inside of cover 10 and ultrasonically welded thereto. Also shown is the interior of first section 28 which, in the preferred embodiment, has a shape, at least on its inside surface, adapted to tightly engage top 22 of ampoule 12. The internal surface of section 28 preferably extends at least about 200° around the outer circumference of top 22. Of course, as long as there is sufficient circumferential envelopment of the outer surface of top 22 to tightly capture the top after neck 24 is fractured, the cover will perform its intended function of moving top 22 away from body 18

Figure 3:
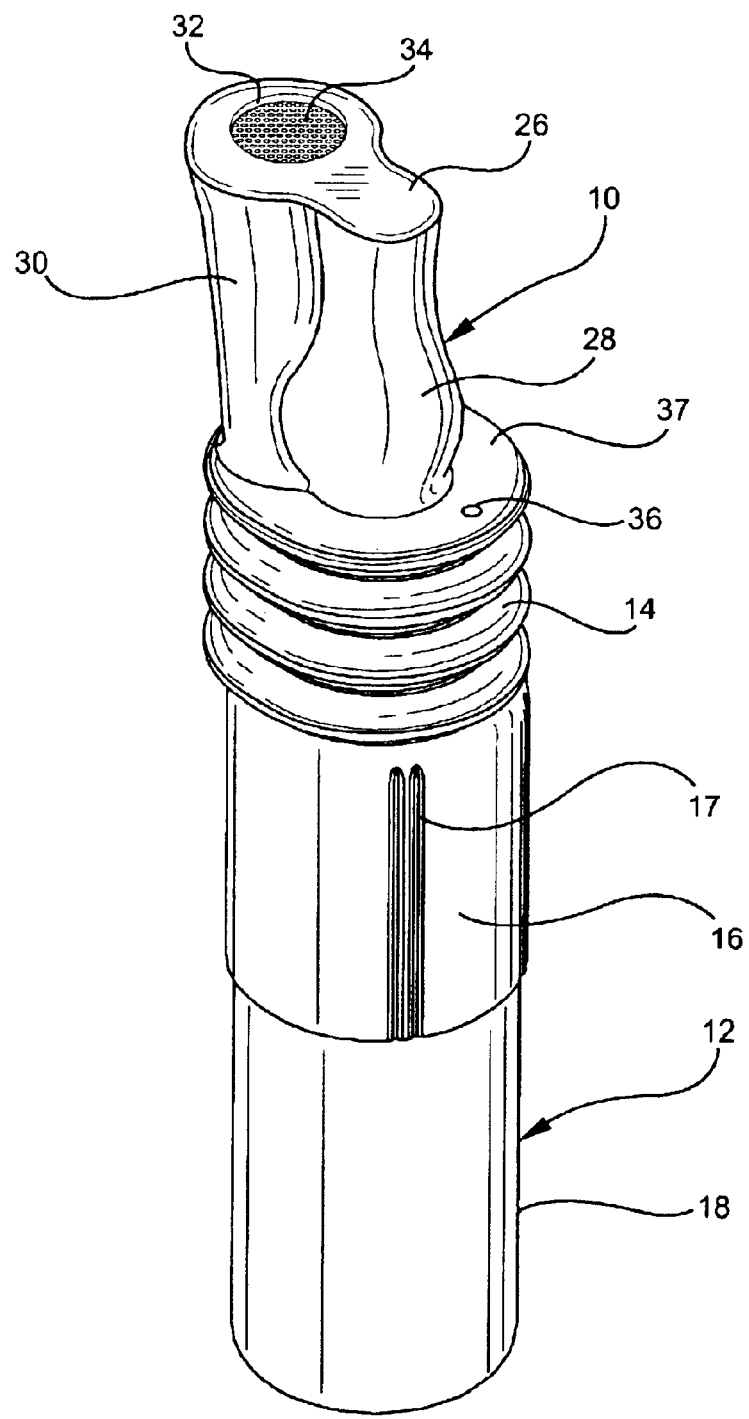
FIG. 3 is a view of the assembled cover and ampoule shown in FIG. 1 with the expandable bellows in its initial expanded position.
Figure 4:
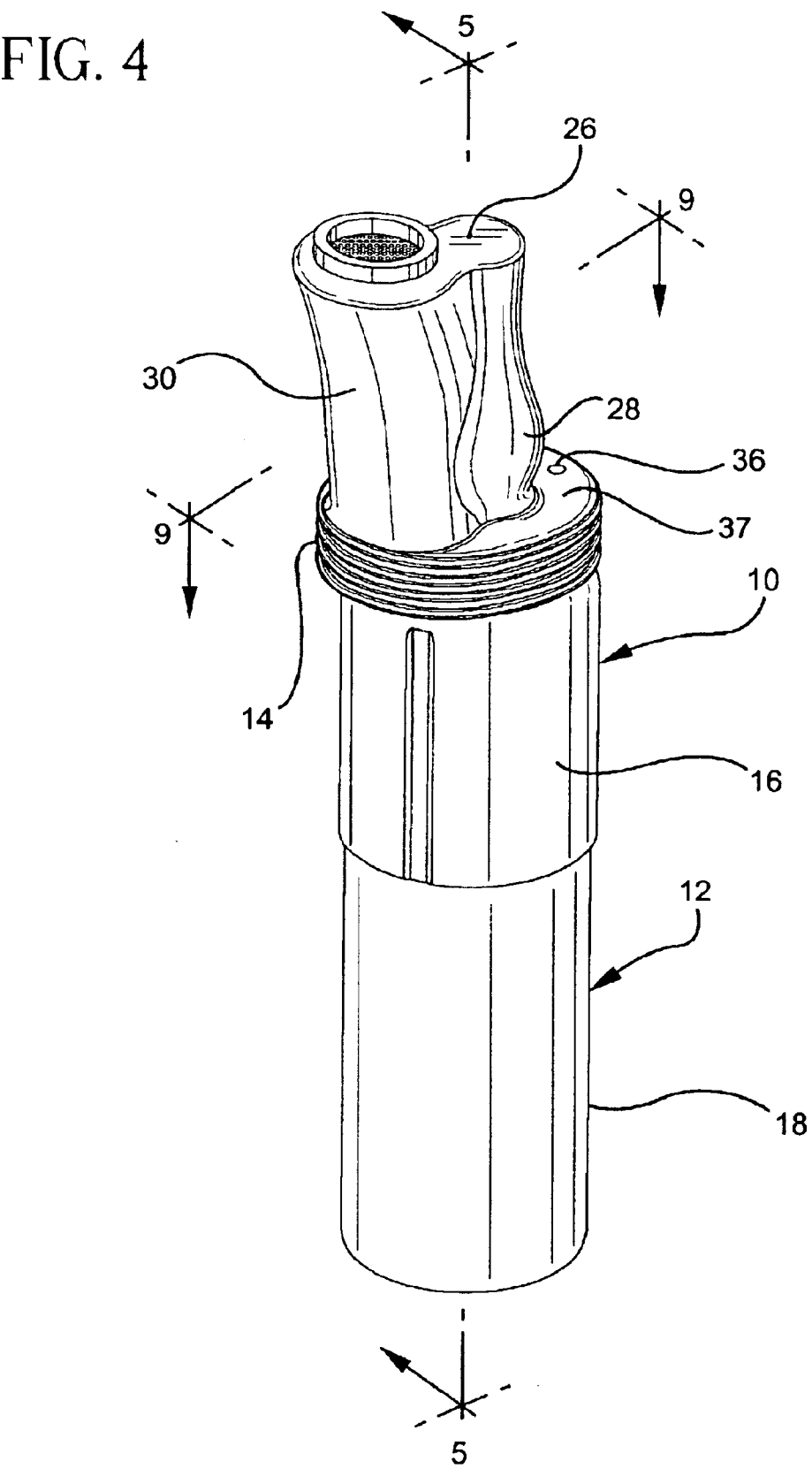
FIG. 4 is the assembled cover and monomer ampoule of FIG. 1 with the expandable bellows in its contracted position after its placement on the top of the ampoule.
Figure 5:
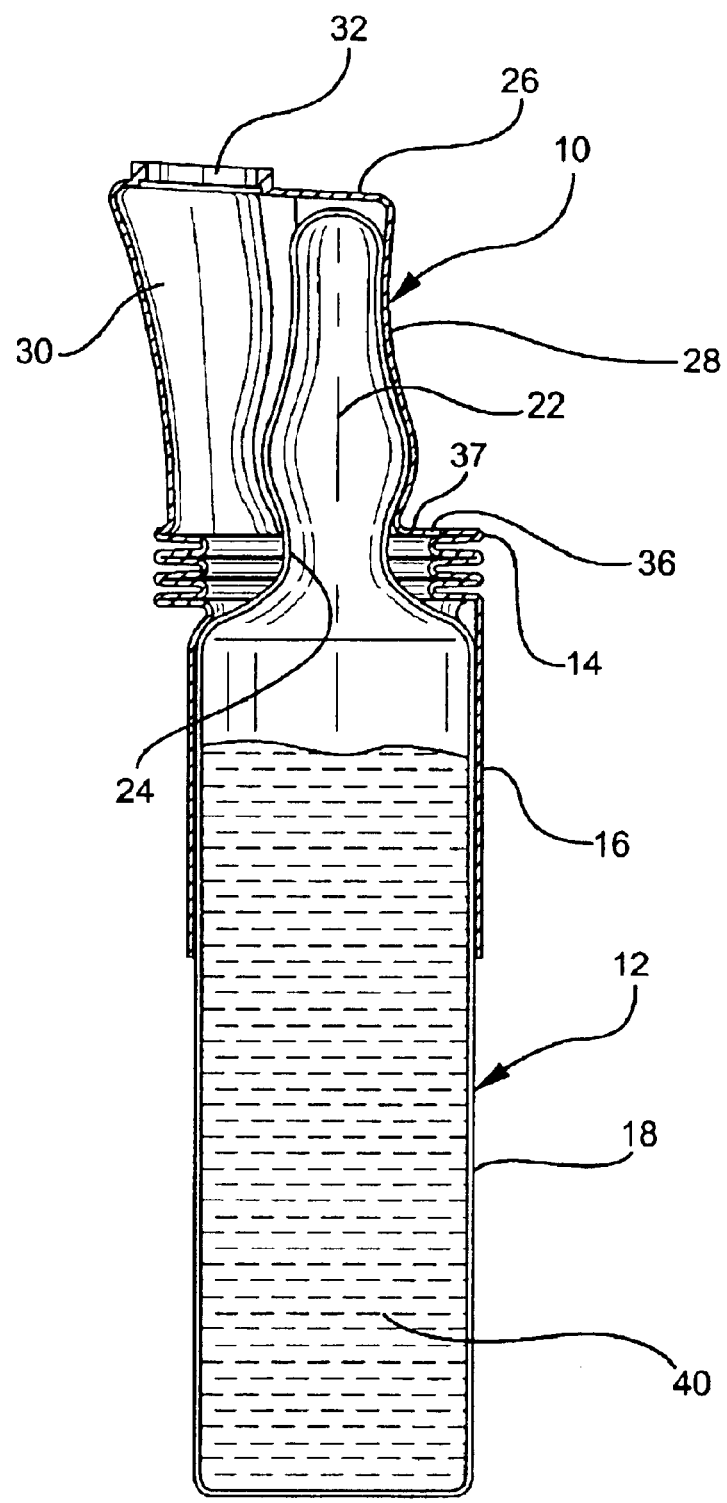
FIG. 5 is a cross-sectional view of the assembled cover and monomer ampoule of FIG. 4 along lines 5—5 thereof.
Figure 6:
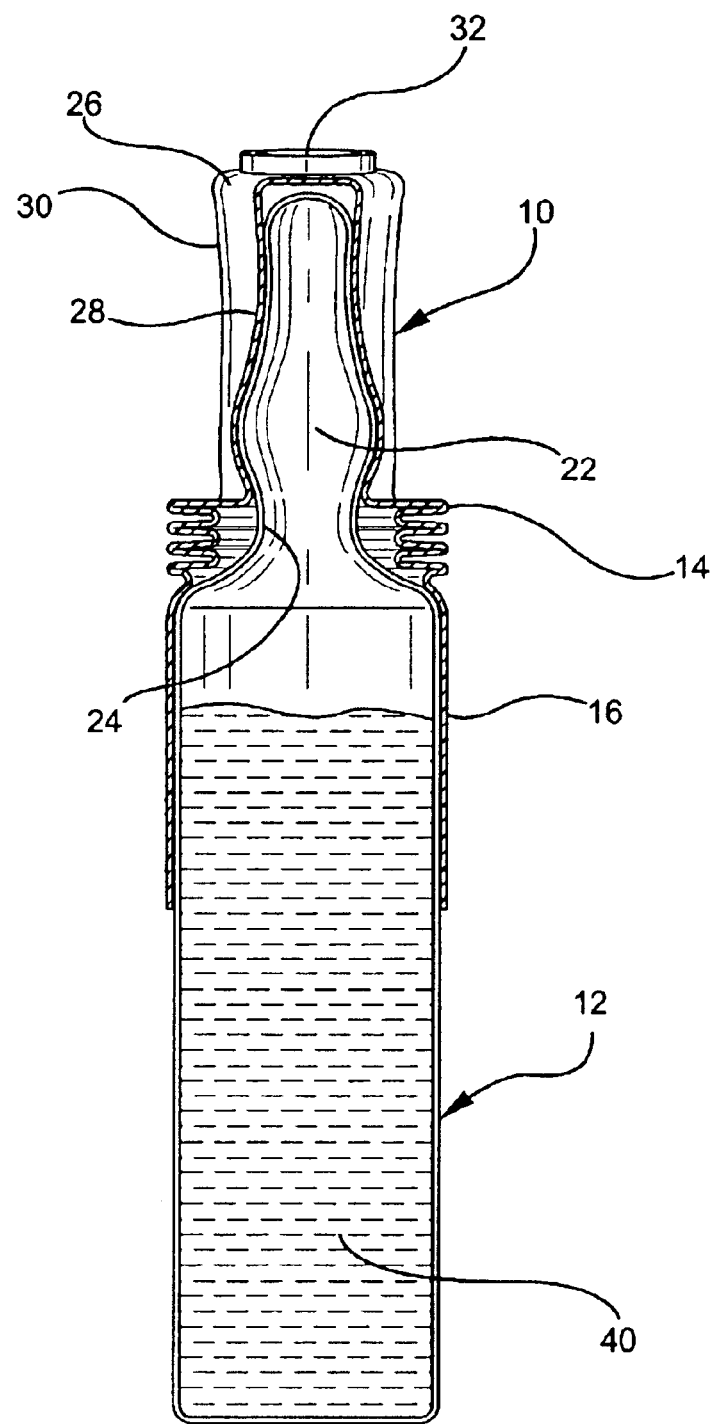
FIG. 6 is a cross-sectional view of the cover and ampoule of FIG. 5 rotated 90°.

Referring to FIG. 3, there is shown cover 10 engaged on body 18 of ampoule 12. This is accomplished by moving the cover in a direction of arrow A of FIG. 1. Once hollow cylindrical portion 16 is fully positioned on surface 20 of body 18, a force can be applied to portion 26 to collapse the bellows and tightly engage section 28 onto top 22. As shown in FIG. 4, the bellows 14 collapses and is held in position by the structural integrity of ampoule 12. Obviously, the expansion force of the bellows cannot alone be sufficient to break neck 24 for the invention to work. Referring to FIGS. 5 and 6, there is shown a sectional view of the cover/ampoule combination of FIG. 4 along lines 5—5. Ampoule 12 includes a fluid 40 which, in the preferred embodiment, is a liquid monomer of a two component bone cement. Again, bellows, or flexible expandable portion 14 is shown in its contracted position and is held therein by the tight engagement with top 22 and section 28 of portion 26 of cover 10.

Figure 7:
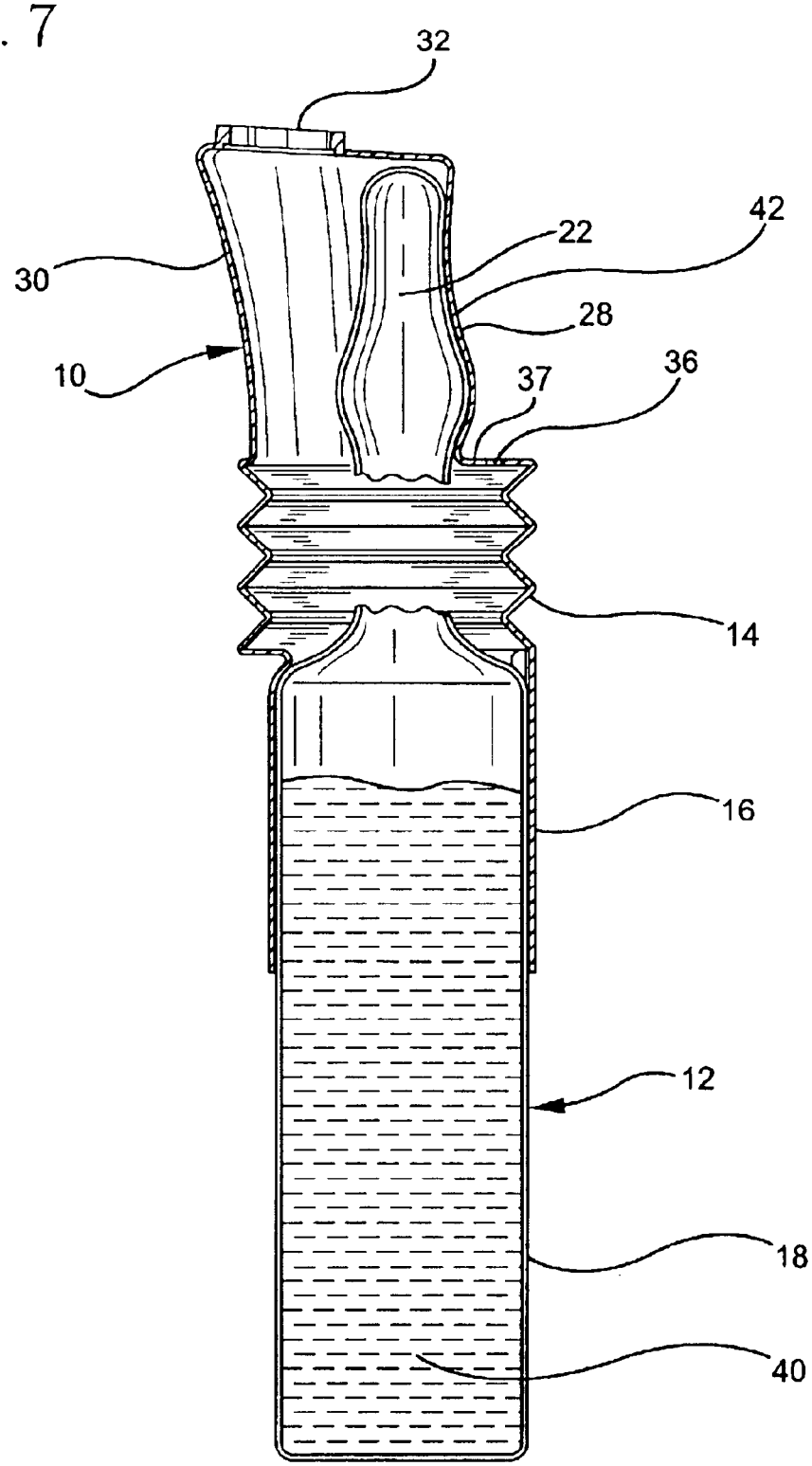
FIG. 7 is a cross-sectional view of the cover and ampoule as shown in FIGS. 5 and 6 with the neck of the ampoule fractured and the bellows again expanded.

Referring to FIG. 7, there is shown the cover and ampoule after top 22 has been broken off of body 18 of ampoule 12 by fracturing the neck of the ampoule. The ampoule neck is designed to be fractured by the user, who grips the assembly in one hand and places his thumb on curved surface 42' of section 28 and applies pressure laterally towards section 30. Alternatively, a mechanical device which can be used to fracture the neck receives top portion 22. The ampoule 12 is designed such that this pressure cracks or fractures neck 24. This allows head or top 22 to be captured within section 28 of cover 10 and to move upwardly as bellows 14 expands to its relaxed position. As can be seen in FIG. 7, head 22 is then spaced from neck 24 a distance equal to the amount of movement of bellows 14 from its contracted to its expanded position. Any flexible design which moves top 22 away from body 18 when the neck is broken can be employed.

Figure 8:
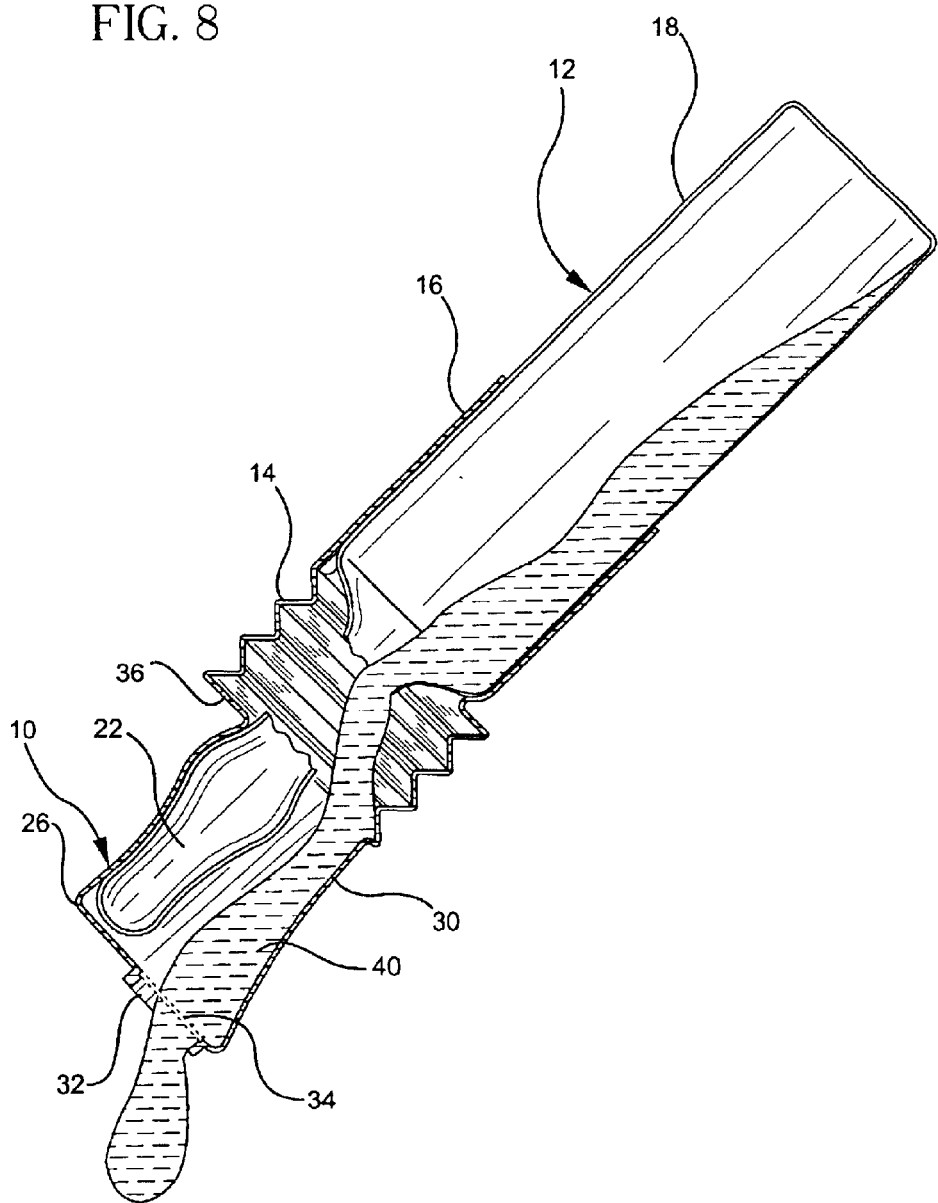
FIG. 8 is a cross-sectional view of the cover and ampoule as shown in FIG. 7 with the fluid from the ampoule being poured out through an opening in the cover.
Figure 9:
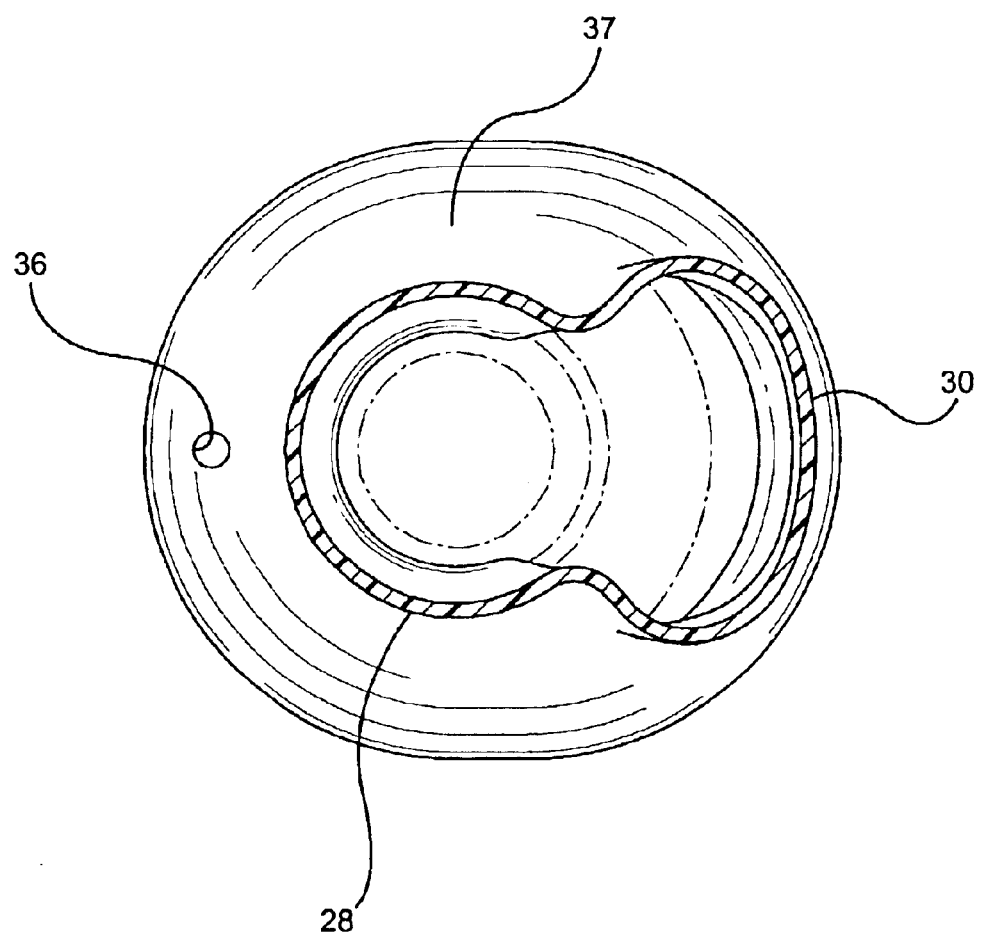
FIG. 9 is a cross-sectional view of the cover shown in FIG. 4 along lines 9—9.

Referring to FIG. 8, there is shown the liquid contents 40, such as liquid monomer, being poured from opening 32 through filter 34. Section 30 of portion 26 acts as a spout to direct the fluid 40 away from the inner cavity of top 22 so that the entire contents of the ampoule 12 may be preferably poured through cover 10. As discussed above, a vent opening 36 is provided in bellows shoulder surface 37. Vent 36 allows air to enter into the emptying interior of ampoule 12. This allows fluid 40 to pour smoothly out of opening 32 in portion 26 of cover 10.

Figure 10:
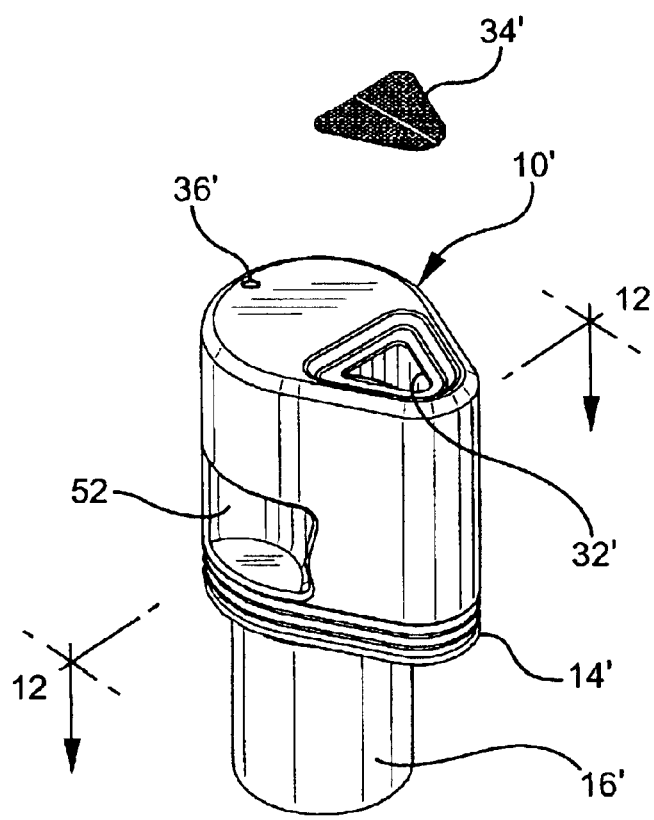
FIG. 10 is an exploded view similar to FIG. 1 of an alternate embodiment of the present invention.
Figure 10:
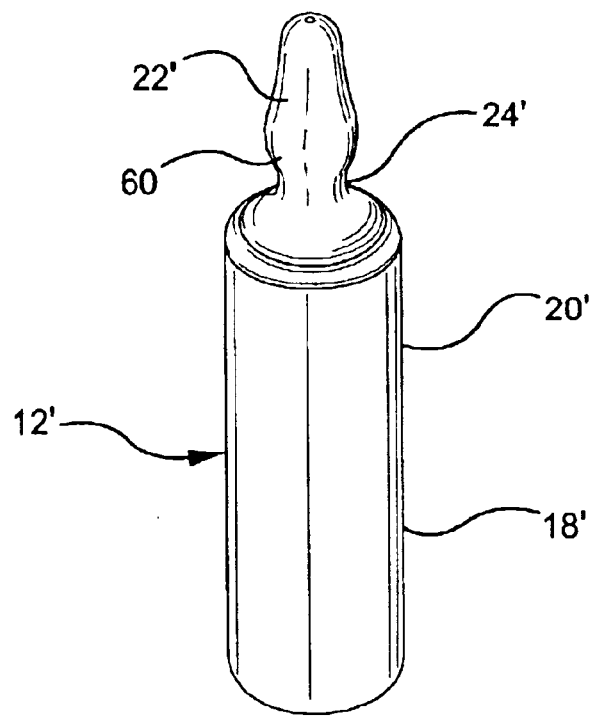
Figure 11:
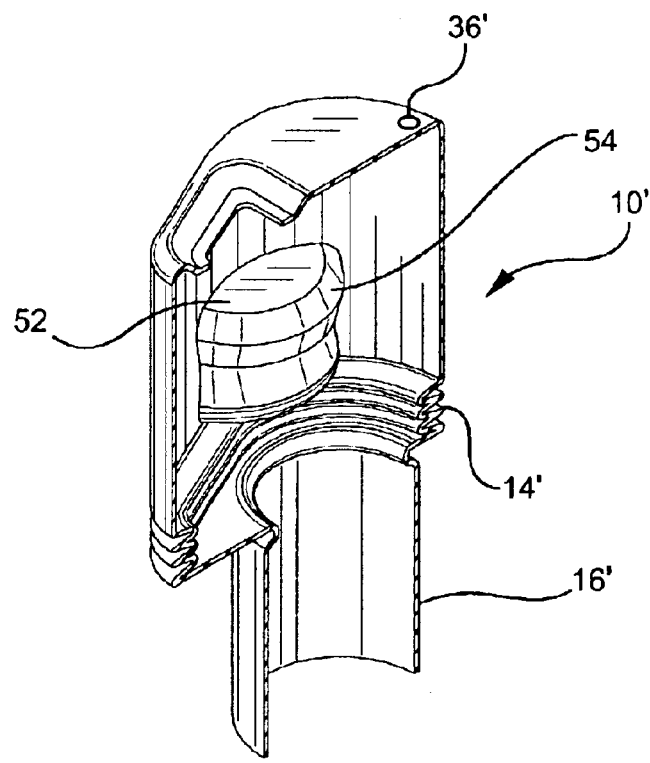
FIG. 11 is a cross-sectional view of the cover shown in FIG. 10.
Figure 12:
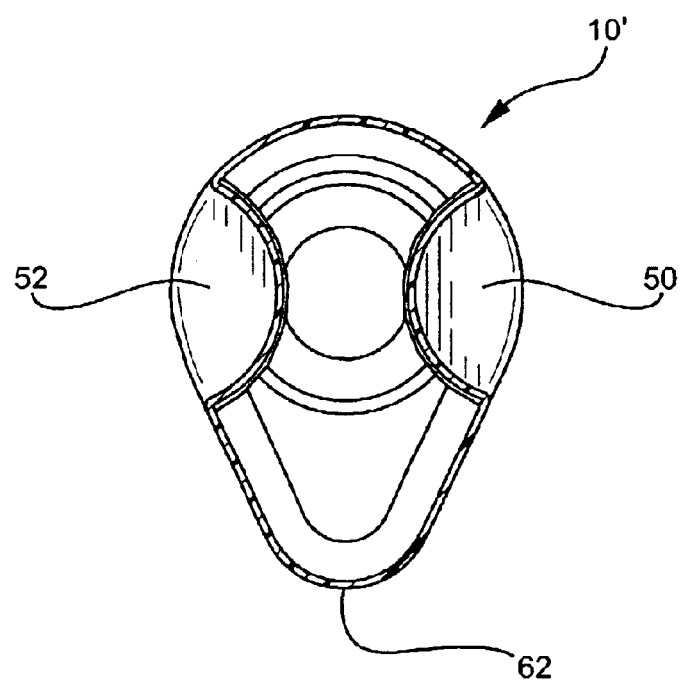
FIG. 12 is a cross-sectional view along lines 12—12 of FIG. 10.

Referring to FIGS. 10–12, there is shown an alternate embodiment for the cover of the present invention generally denoted as 10'. Cover 10' is similar to cover 10 with the exception that it is of a generally triangular shape with a generally triangular opening 32' and a generally triangular screen or mesh 34'. As with screen or mesh 34, mesh 34' is made of a fine metal screen or fabric mesh. In addition, the section of the upper cover portion 26' which grips the ampoule head, 22 is located in the center of the cover. Again, cover 10' has a cylindrical portion 16' adapted to tightly engage the outer surface 20' of ampoule body 18'. As can best be seen in FIGS. 11 and 12, cover 10' again is blow molded from a polyethylene or ethylene vinyl acetate material and includes two recessed areas 50 and 52 which surrounds sides of neck 24' and engage the neck area 24' below head 22'. Depressions 50, 52 have a surface 54 which can be slid over the curve portion 58 of ampoule top 22' so that depressions 50, 52 can be laterally expanded over top 22' and surface 54 engages the lower curved surface 60 of head 22' and prevents the contracted portion 14' from expanding until the neck 24' of the ampoule 12' is fractured. Once neck 24' is fractured, bellows 14' expands moving top 22' away from body 18' allowing the liquid contents of the ampoule 12' to flow out of opening 32' through mesh or filter 34'. The apex of generally triangular shape of the alternate cover 10' forms a spout area 62 to ease the pouring of the liquid contents of ampoule 12' out of opening 32'.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A device for fracturing the neck of a glass ampoule of the type having a body, a top and neck joining the body and the top and dispensing fluid therefrom, the device comprising:
   a first portion having an interior sized to sealingly engage an exterior surface of the body of the ampoule;
   a second portion having a first hollow interior section sized to capture the top of the ampoule, said second portion having a second interior section communicating with a neck area of the ampoule, said second section including an opening; and
   a flexible portion connecting the first and second portions, the flexible portion capable of moving the ampoule head away from the neck area of the ampoule.

2. The device as set forth in claim 1 wherein the flexible portion is an expandable portion.

3. The device as set forth in claim 2 wherein the expandable portion has a contracted position when said ampoule top is connected to said body by said neck and an expanded position after said neck is broken.

4. The device as set forth in claim 1 wherein the opening includes a filter.

5. The device as set forth in claim 1 wherein said ampoule top captured in the first interior section of the second portion is moved away from the ampoule body as an expandable portion expands after said ampoule neck is broken and wherein the second interior section of the second portion is in the form of a pour spout.

6. The device as set forth in claim 5 wherein said expandable portion connects said first portion to both the first and second interior sections of said second portion.

7. The device as set forth in claim 1 wherein the device is made from a polymeric material.

8. The device as set forth in claim 7 wherein the polymeric material is polyethylene or ethylene vinyl acetate.

9. The device as set forth in claim 1 wherein said first interior section of said second portion has a shape generally conforming to the shape of the ampoule top to capture said top therein.

10. The device as set forth in claim 1 wherein said second interior portion of said second section is radially outwardly offset from a central axis of said ampoule.

11. The device as set forth in claim 1 further including at least one vent hole communicating with said flexible portion and said second interior section.

12. The device as set forth in claim 11 wherein said vent is located on a shoulder connecting said flexible and second portions.

13. A system for delivering liquid agents from a breakable ampoule comprising:

a liquid containing ampoule having a top, a body and a breakable neck connecting the top and body;

a hollow cover having at a first end, a first portion for receiving and sealingly engaging the ampoule body, the cover having at a second end a second portion receiving said ampoule top, a third portion communicating with a neck area of the; ampoule and having an opening at the second end of said cover for dispensing the liquid in the ampoule and a moveable portion connecting the first and second portions, said moveable portion moving from a first position to a second position upon breaking the breakable neck.

14. The system as set forth in claim 13 wherein the opening includes a filter.

15. The system as set forth in claim 13 wherein said moveable portion is a resiliently expandable portion which expands from a contracted to an expanded position when said neck is broken.

16. The system as set forth in claim 15 wherein the expandable portion is a bellows and said ampoule top is captured in the second portion and moved away from said ampoule body as said expandable bellows expands after said ampoule neck is broken.

17. The system as set forth in claim 15 wherein said expandable portion connects said first cover portion to both the second and third cover portions.

18. The system as set forth in claim 15 wherein the cover is made from a polymeric material.

19. The system as set forth in claim 18 wherein the polymeric material is polyethylene or ethylene vinyl acetate.

20. The system as set forth in claim 15 wherein said second portion has a first interior section having a shape generally conforming to a shape of said ampoule top to capture said top therein.

21. The system as set forth in claim 20 wherein said second portion has a second interior including said opening section positioned radially outwardly from a central axis of said ampoule.

22. The system as set forth in claim 15 wherein said cover includes at least one vent hole communicating with said expandable portion and said third portion.

23. The system as set forth in claim 22 wherein said vent hole is located on a shoulder connecting said expandable and second portions.

24. A method for dispensing a fluid from a breakable fluid containing ampoule having a top, a body and a breakable portion connecting the top and body comprising:

placing a cover over the ampoule, the cover having a first portion for receiving the ampoule body, a second portion for receiving the ampoule top and a third portion located between said first and second portions for moving the ampoule top away from the ampoule body after the breakable portion is broken;

applying a force against the second portion of the cover to break the breakable portion of the ampoule;

moving the ampoule top portion away from the ampoule body by the action of the third cover portion; and dispensing the fluid from the ampoule through an opening in said cover.

25. The method as set forth in claim 24 wherein the third portion is an expandable portion connected between the first and second portions which expands from a contracted state to an expanded state when the breakable portion is broken.

26. The method as set forth in claim 25 wherein the ampoule body has a generally cylindrical shape and the first portion of the cover has a generally cylindrical hollow interior for sealingly engaging the ampoule body.

27. The method as set forth in claim 26 wherein the second portion includes a first section for capturing the ampoule head and a second section in fluid communication with the breakable portion of the ampoule so that upon breaking the breakable portion the fluid may be poured from the ampoule through the opening.

28. The method as set forth in claim 27 wherein said opening is covered by a filter.

* * * * *

UNITED STATES PATENT AND TRADEMARK OFFICE
CERTIFICATE OF CORRECTION

PATENT NO. : 6,832,703 B1
DATED : December 21, 2004
INVENTOR(S) : Christopher Scott and Anthony J. LaRosa It is certified that error appears in the above-identified patent and that said Letters Patent is hereby corrected as shown below:

Column 3,
Line 15, "1800" should read -- 180° --.

Column 4,
Line 53, "td" should read -- to --.

Column 5,
Line 9, after "section" delete -- : --.
Line 33, after "bellows" delete -- , --.
Line 40, after "42" delete -- ' --.

Column 6,
Line 3, after "head" delete -- , --.

Column 7,
Line 19, after "the" delete -- ; --.

Signed and Sealed this

Nineteenth Day of April, 2005

JON W. DUDAS
*Director of the United States Patent and Trademark Office*